US009725315B2

(12) United States Patent
Austin et al.

(10) Patent No.: US 9,725,315 B2
(45) Date of Patent: Aug. 8, 2017

(54) NANOCHANNEL ARRAYS AND NEAR-FIELD ILLUMINATION DEVICES FOR POLYMER ANALYSIS AND RELATED METHODS (75) Inventors: Michael Austin, Philadelphia, PA (US); Parikshit A. Deshpande, Princeton, NJ (US); Alexey Sharonov, Drexel Hill, PA (US); Valeriy Bogdanov, Philadelphia, PA (US)

(73) Assignee: BIONANO GENOMICS, INC., San Diego, CA (US)

( * ) Notice: Subject to any disclaimer, the term of this patent is extended or adjusted under 35 U.S.C. 154(b) by 1403 days.

(21) Appl. No.: 13/498,846

(22) PCT Filed: Sep. 27, 2010

(86) PCT No.: PCT/US2010/050362
§ 371 (c)(1),
(2), (4) Date: Jun. 13, 2012

(87) PCT Pub. No.: WO2011/038327
PCT Pub. Date: Mar. 31, 2011

(65) Prior Publication Data
US 2012/0244635 A1   Sep. 27, 2012

Related U.S. Application Data (60) Provisional application No. 61/246,251, filed on Sep. 28, 2009.

(51) Int. Cl.
*G01N 33/558* (2006.01)
*B82Y 30/00* (2011.01)
*G01N 21/64* (2006.01)

(52) U.S. Cl.
CPC ............ *B82Y 30/00* (2013.01); *G01N 21/645* (2013.01); *G01N 33/558* (2013.01)

(58) Field of Classification Search
None
See application file for complete search history.

(56) References Cited

U.S. PATENT DOCUMENTS 6,917,726 B2   7/2005   Levene et al.
7,555,159 B2   6/2009   Pishva
(Continued)

FOREIGN PATENT DOCUMENTS

CN           101516512 A       8/2009
WO     WO 03/010289 A2       2/2003
(Continued)

OTHER PUBLICATIONS

Liu et al., "Surface plasmon interference nanolithography", Nano Letters, vol. 5, issue 5, pp. 957-961 (2005).
(Continued)

*Primary Examiner* — Chris L Chin
(74) *Attorney, Agent, or Firm* — Knobbe, Martens, Olson & Bear, LLP (57) ABSTRACT Provided are devices and methods for polymer analysis, in which labeled polymers are translocated along nanochannels that have illuminated detection regions within. As a labeled polymer translocates along the nanochannel and the labels pass over the illuminated detection regions, the labels become detectable (e.g., where different labels fluoresce in response to different wavelengths present at different illumination regions), and the user generates a spatial map of the location of the various labels along the length of the polymer. The location of the labels is then correlated to one or more structural characteristics of the polymer.

32 Claims, 9 Drawing Sheets (56) References Cited

U.S. PATENT DOCUMENTS

2004/0197843 A1 10/2004 Chou et al.
2008/0242556 A1 10/2008 Cao et al.

FOREIGN PATENT DOCUMENTS

WO     WO 2008/121828       10/2008
WO     WO 2011/038327 A1   3/2011

OTHER PUBLICATIONS

Office Action dated Dec. 20, 2013 in Chinese Patent Application No. 201080043518.3.
Palamaru et al., "Sub-Wavelength Metallic Gratings of Very High Transmission Efficiency," Journal of Optoelectronics and Advanced Materials, vol. 1, No. 2, pp. 35-40 (1999).
Office Action dated Apr. 1, 2013 in Chinese Application No. 201080043518.3.
International Search Report dated Jan. 31, 2011 for International Application No. PCT/US10/50362, filed Sep. 27, 2010.
Written Opinion dated Jan. 31, 2011 for International Application No. PCT/US10/50362, filed Sep. 27, 2010.
Levene, et al.: "Zero-Mode Waveguides for Single-Molecule Analysis at High Concentrations", Science, vol. 299, Jan. 31, 2003, pp. 682-686.
Ebbesen et al: "Extraordinary Optical Transmission Through Sub-Wavelength Hole Arrays", Nature, vol. 391, Feb. 12, 1998, pp. 667-669.
Decision of Rejection dated Jun. 30, 2014 in Chinese Application No. 201080043518.3.
Third Office Action dated May 20, 2016 in Chinese patent application No. 201080043518.3.
Fourth Office Action dated Nov. 15, 2016 in Chinese patent application No. 201080043518.3.

NANOCHANNEL ARRAYS AND NEAR-FIELD ILLUMINATION DEVICES FOR POLYMER ANALYSIS AND RELATED METHODS

RELATED APPLICATIONS

The present application is a U.S. national phase under 35 U.S.C. §371 of International Application No. PCT/US2010/050362, entitled NANOCHANNEL ARRAYS AND NEAR-FIELD ILLUMINATION DEVICES FOR POLYMER ANALYSIS AND RELATED METHODS, filed Sep. 27, 2010, and published on Mar. 31, 2011 as WO/2011/038327, which claims the benefit of U.S. Provisional Patent Application No. 61/246,251, filed on Sep. 28, 2009. The content of each of these related applications are hereby incorporated by reference in their entirety.

TECHNICAL FIELD

The present invention relates to the field of nanofluidics and to the field of macromolecular analysis.

BACKGROUND

There has been increasing interest regarding the relationship between the structure of genetic material (e.g., nucleic acid polymers) and the expression (or possible expression) of physiological characteristics related to that structure. Accordingly, there is a need in the art for devices and methods capable of quickly and efficiently gathering such structural information. The value of these devices and methods would be further enhanced if they were capable of efficiently comparing the structures of multiple samples.

SUMMARY

In meeting the described challenges, the present invention first provides analysis devices, comprising a plurality of nanochannels running along the surface of a first substrate, each nanochannel defined by side walls and a floor; and at least one nanoslit being disposed in a second substrate, the nanoslit being disposed such that electromagnetic radiation of at least a first wavelength passing through the nanoslit defines, within the at least one nanochannel, an illumination region having a cross-sectional dimension smaller than the first wavelength.

The present invention also provides analysis devices, comprising a plurality of nanochannels running along the surface of a first substrate, each nanochannel being defined by side walls and a floor, a phase mask disposed about at least one nanochannel such that electromagnetic radiation of at least a first wavelength passing through the phase-shift mask defines, in the at least one nanochannel, an illumination region within the at least one nanochannel, the illumination region having a cross-sectional dimension smaller than the first wavelength.

Also provided are methods of analysis, comprising translocating a macromolecule comprising two or more labels through two or more excitation regions along one or more nanochannels; exciting the labels within the excitation regions with electromagnetic radiation to give rise to one or more signals, the excitation regions being characterized as having a cross-sectional dimension smaller than the wavelength of the electromagnetic radiation; and correlating the one or more signals to the relative positions of the labels along the macromolecule.

BRIEF DESCRIPTION OF THE DRAWINGS

The summary, as well as the following detailed description, is further understood when read in conjunction with the appended drawings. For the purpose of illustrating the potential embodiments, there are shown in the drawings various exemplary embodiments; however, the potential embodiments are not limited to the specific methods, compositions, and devices disclosed. In addition, the drawings are not necessarily drawn to scale. In the drawings.

DETAILED DESCRIPTION OF ILLUSTRATIVE EMBODIMENTS

The potential embodiments are not limited to the specific devices, methods, applications, conditions or parameters described and/or shown herein, and that the terminology used herein is for the purpose of describing particular embodiments by way of example only and is not intended to be limiting. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Features of the potential embodiments which are, for clarity, described herein in the context of separate embodiments, may also be provided in combination in a single embodiment. Conversely, various features of the potential embodiments that are, for brevity, described in the context of a single embodiment, may also be provided separately or in any subcombination. Further, reference to values stated in ranges include each and every value within that range.

This invention provides, inter alia, polymer analysis systems and methods based on a nanochannel array and a near-field illuminator array matrix device. The nanochannel array (e.g., U.S. patent application Ser. No. 10/484,793, incorporated herein by reference in its entirety) is suitably an array of nanochannels in which polymer molecules are linearly flowed such that only one polymer molecule occupies a section of a nanochannel at a time. The nanochannels are suitably dimensioned so as to at least partially elongate macromolecules translocated within the nanochannels, e.g., by entropic confinement.

Figure 1:
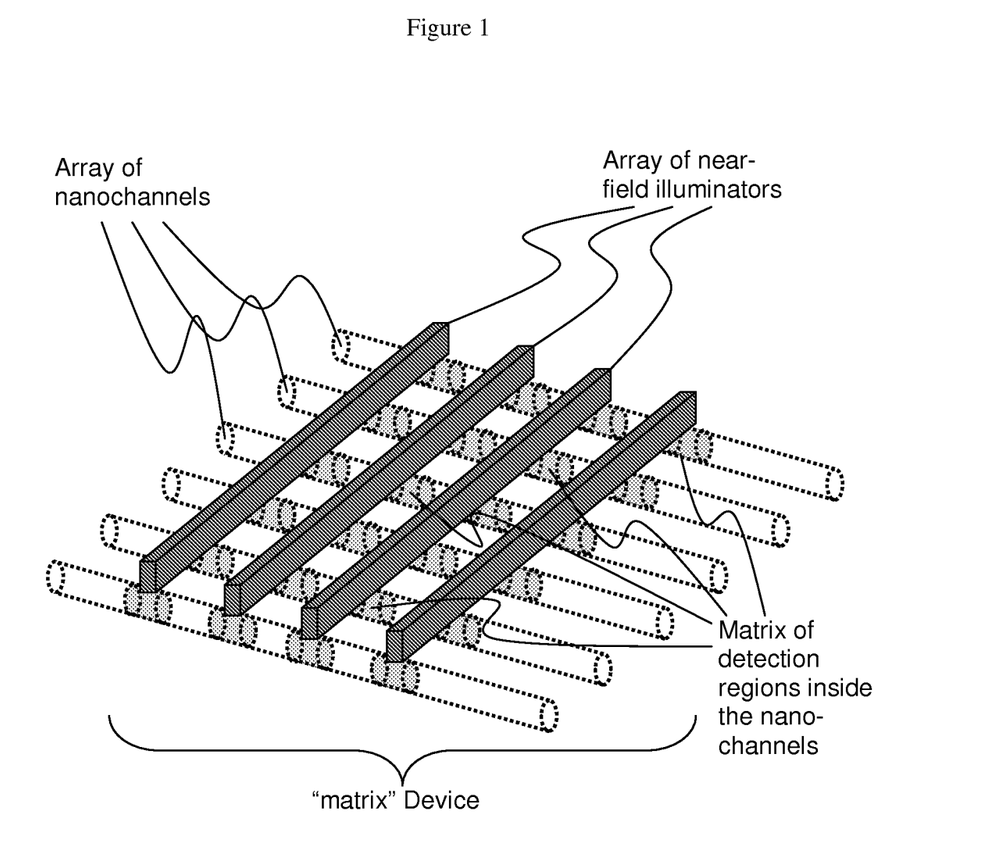
FIG. 1 depicts an array of nanochannels fabricated over/under an array of near-field illuminators, producing multiple matrix detection locations at their intersection—as a polymer labeled with fluorescent bodies flows through a nanochannel, the fluorescent body will be excited by the illuminator at the matrix detection locations, and this signal will be detected.

In one embodiment, the present invention incorporates an additional device that produces an array of near-field illuminators over/under the nanochannels, as shown in non-limiting FIG. 1, which figure depicts nanochannels and a corresponding set of near-field illuminators that give rise to a matrix of detection regions disposed within the nanochannels. The sections of the nanochannel array which lie proximate (e.g., under, over, or both) the near-field illuminators form a matrix of detection regions.

The detection regions are defined such that illumination of the body of interest in the nanochannels occurs within these regions, and the regions are suitably are lengthwise spatially smaller than the wavelength of the light being used. Preferably, the region of illumination is smaller than the diffraction limit of the wavelength of the light being used. This is shown by, e.g., FIG. 1, described in more detail elsewhere herein.

In one embodiment, the polymer molecules are labeled with bodies that fluoresce when they pass under/over the near-field illuminators, as shown by non-limiting FIGS. 2, 7, 8, and 9.

The fluorescent bodies can be virtually any species that is detectable when exposed to a particular wavelength of light. Fluorophores (fluorescein, Texas Red, YOYO, BODIPY-FL, and the like) are especially suitable. The labels are suitably configured so as to bind specifically to a particular structural motif on a polymer/macromolecule, so as to permit the user to locate that motif with a degree of certainty on a macromolecule or on different macromolecules.

As one non-limiting example, a user may chose a first label that fluoresces when exposed to light of exemplary wavelength X. The first label is also configured so that it binds specifically to a particular first sequence of nucleic acids. This may be accomplished by conjugating the label to one or more nucleic acids or other species that are complementary to the first sequence of nucleic acids. In this way, a fluorophore can be used to detect the presence of one, two, or more nucleic acids (or other units) present in a particular sequence within a polymer sample, by selecting the "linker" group or groups to which the fluorophore is attached.

Figure 2:
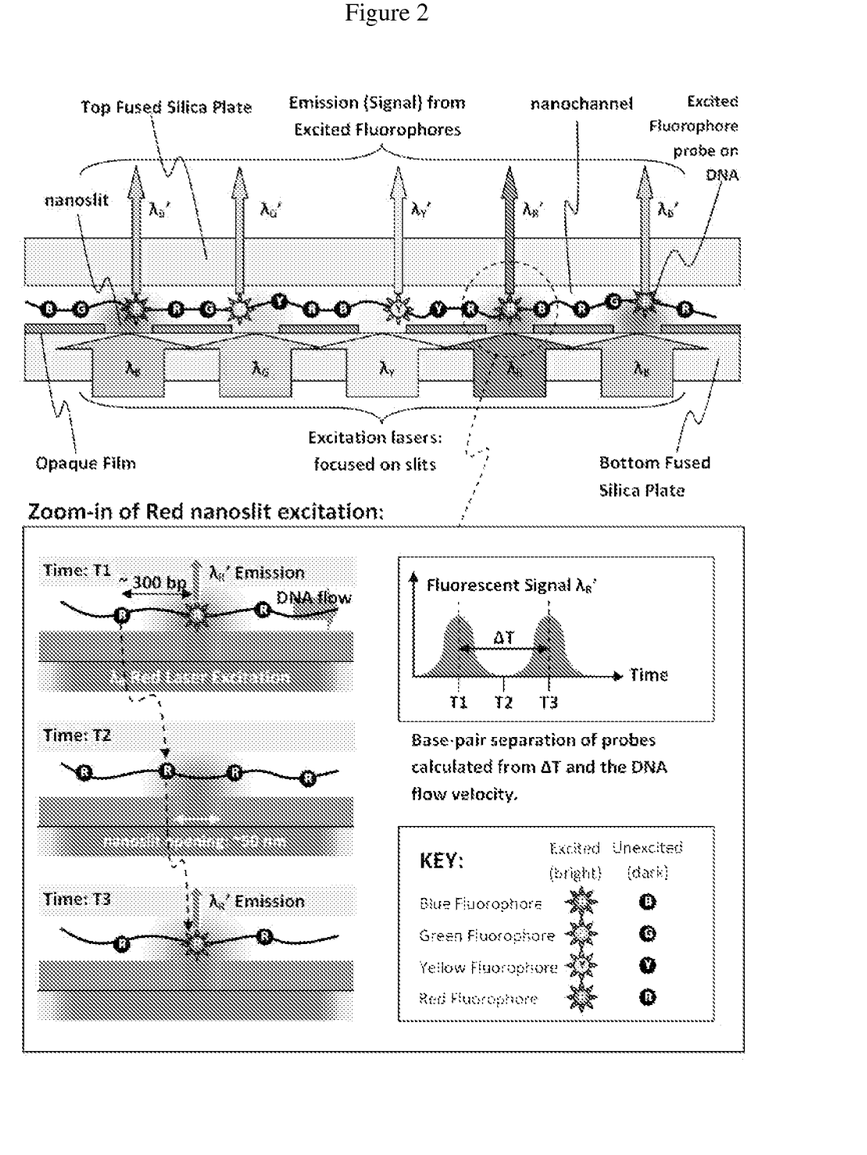
FIG. 2 depicts a non-limiting, nanoslit-based embodiment of a near-field illuminator array, which includes 5 slits, 1 for each color, except for blue which has two slits—the two blue slits are used to determine the velocity of the polymer molecule as it flows through the channel and over the slits, and the slits confine the near-field illumination to narrow (sub-100 nm) region of the nanochannel. In this embodiment, the polymer is a DNA molecule labeled with 4 different color fluorophores, and when the appropriate fluorophore travels over the illuminated slit (matrix detection region), it becomes excited and emits a fluorescent signal, and a spatial map of the fluorescent labels along the DNA can be determined by software using the measured velocity.
Figure 7:
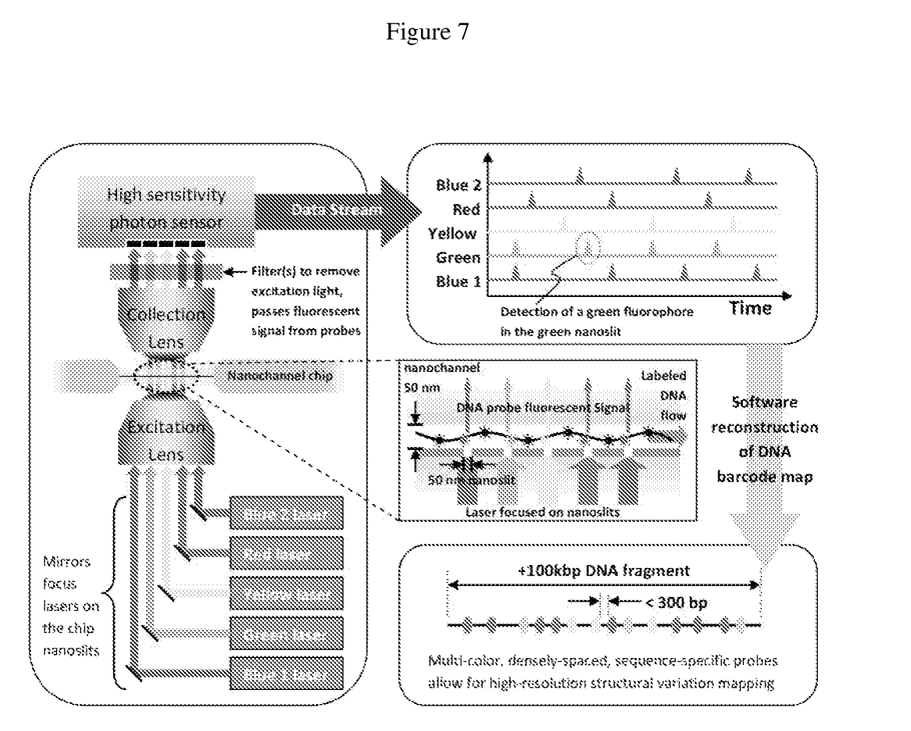
FIG. 7 illustrates exemplary signal detection and analysis, in which lasers are focused as lines on the bottom of the chip's nanoslits, fluorescently exciting the probes on the DNA as it passes over the nanoslits as it flows through one of the nanochannels, and the excited fluorescent signals are detected giving a temporal bar-code signature for each matrix detection region that the DNA passes through, the signals being translated into a spatial bar-code of the DNA.
Figure 8:
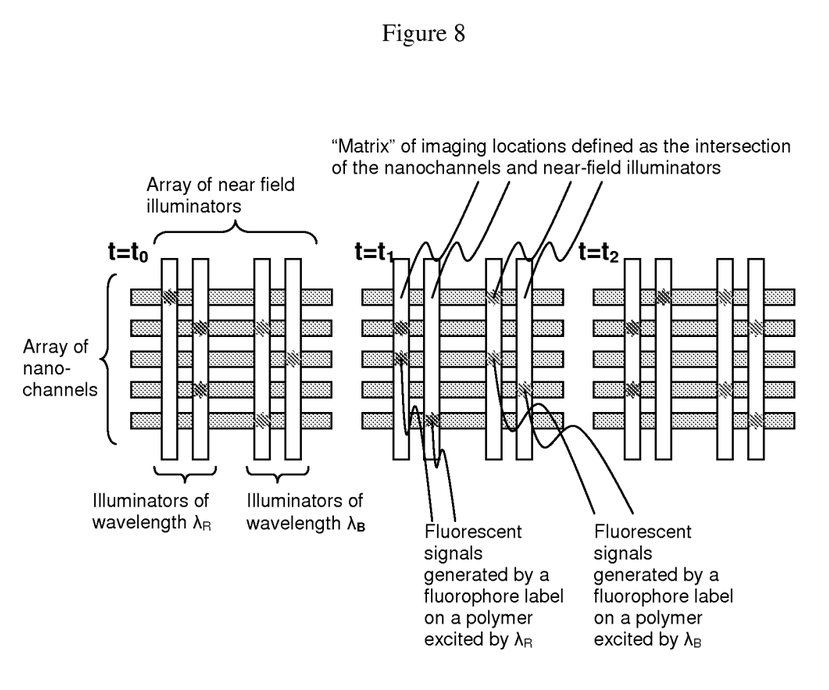
FIG. 8 depicts a matrix device having two wavelengths of illumination shown at 3 different successive time intervals t0, t1, and t2—each detection region generates a temporal signal that represents labels of a specific fluorophore passing that region in time.

The user may also choose a second label that fluoresces when exposed to light of exemplary wavelength Y. The second label is also configured so that it binds specifically to a particular second sequence of nucleic acids. This may be accomplished by conjugating the label to one or more nucleic acids or other species that are complementary to the second sequence of nucleic acids. In this way, the user can then label those regions of the macromolecule that contain the first and second sequences of nucleic acids, and then visualize those labels when the labels are exposed to illumination of wavelengths X and Y, as shown in FIGS. 2, 7, and 8.

As shown, the labels' signals are detected and correlated to one or more characteristics of the macromolecule under study. Each body/label is detected at multiple times as it passes through multiple near-field illuminators, which allows for the transit velocity of the fluorescent body to be determined. In this way a polymer labeled with fluorescent labels can have a spatial map ("bar-code") of the labels on the polymer generated by monitoring the temporal signals from the matrix detection regions and then reconstructing the map with software, shown by non-limiting FIG. 7. As the near-field illuminator only illuminates a narrow region of the channel, the spatial resolution of the bar-code map can be less than the diffraction limit of the illuminating light. This has many useful applications, as described elsewhere herein.

Figure 9:
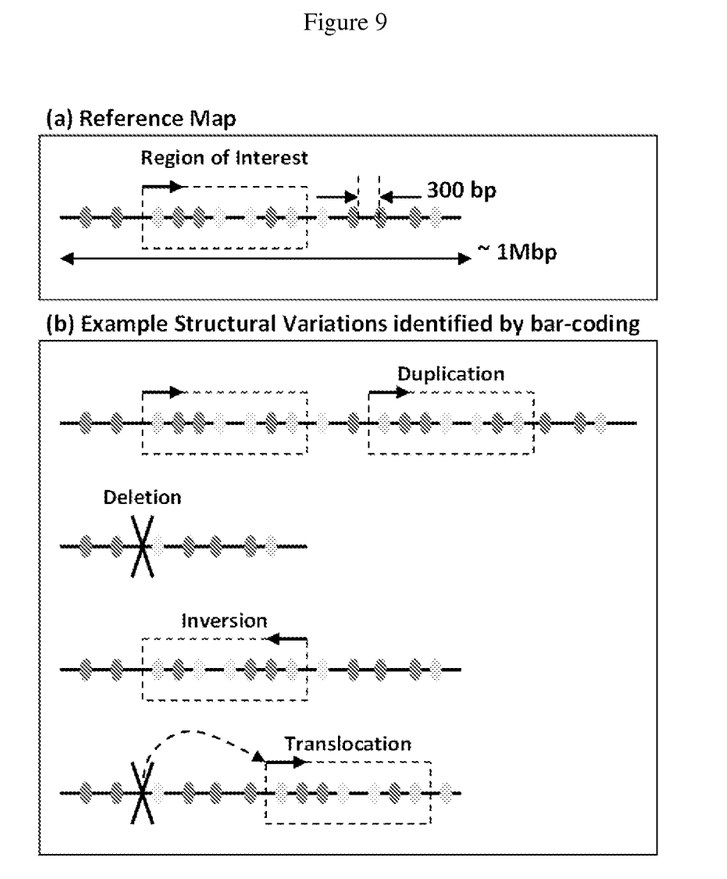
FIG. 9 depicts using barcoding according to the disclosed invention to identify structural variations in a nucleic acid biopolymer (DNA).

The array of near-field illuminators can be comprised of more than one wavelengths of electromagnetic radiation. These wavelengths are chosen such that each wavelength excites a particular fluorophore (see FIGS. 2, 7, and 8). In this way, a multi-color bar-code spatial map can be generated for a given macromolecule under analysis, as shown in FIG. 9.

As shown in that figure, the user can, using the claimed invention, generate a reference map of a region (or regions) of interest on a macromolecule. This region of interest may relate to, e.g., a gene (or portion thereof) related to the expression of a particular protein, or may otherwise be a marker for a particular physiological characteristic. Once the reference map has been obtained, the user may identify, on a macromolecule, duplicate/multiple locations of the reference map, deletions of the reference map, inversions of the reference map, or translocations of the reference map. In this way, the user may analyze and compare multiple samples against one another so as to determine whether particular members of a sample population possess the region of interest, or whether certain members possess some variation of that region. These variations, deletions, inversions, and even translocations can, as described elsewhere herein, evidence a physiological or disease state, or even a predisposition to such a state.

Example Embodiment: Nanoslit Near-Field Illuminator

In one embodiment, an array of near-field illuminators are generated by patterning an array of nano-slits under/over the nanochannels, as shown in FIG. 2. These slits are suitably made in metal. The slit opening is preferably about 1-500 nm wide, but can also be in the range of from 1 about 300 nm, from 10 to about 100 nm, or even about 15 nm.

As shown in FIG. 2, a sample array includes 5 slits, 1 for each color, except for blue (shown at the far left and far right of the figure), which color has two slits. (The two blue slits are used to determine the velocity of the polymer molecule as it flows through the channel and over the slits.)

The slits confine the near-field illumination to narrow (sub-100 nm) regions of the nanochannel. In the present figure, the macromolecule is a DNA molecule labeled with 4 differently colored fluorophores. When the appropriate fluorophore travels past the illuminated slit (matrix detection region), the fluorophore becomes excited and emits a fluorescent signal. A spatial map of the fluorescent labels along the DNA is suitably generated by software using the measured velocity of the DNA through the device's detection regions.

The concept of this embodiment is to limit the transmission of light through a narrow slit by making the slit composed of an opaque material with an opening far smaller than the wavelength of the illumination light (FIG. 2). The evanescent field of the illumination light will only extend a few 10 s of nm laterally from the slit opening directly above the slit, thus providing a very narrow region of the nanochannel (<100 nm) in which the illumination light is present.

As shown in the non-limiting figures, DNA polymer fragments bearing fluorescent probes are elongated and streamed through the nanochannels and over the nanoslits. The narrow height of the nanochannels (e.g., about 50 nm, in some embodiments) ensures the macromolecule's probes are sufficiently close to the nanoslit opening to be excited when the probe/fluorophore passes over the slit. Because the excitation light is physically confined to a small area (<100 nm), the fluorophores are individually detected on that length scale, thus overcoming the diffraction resolution limit that has limited other detection devices. The channels may have a height of 10 nm, 50 nm, 100 nm, 200 nm, 500 nm, or even 1 micrometer, in some embodiments.

In this particular embodiment, at least one wavelength of light suitably has at least 2 slits associated with it such that these two slits can be used to determine the velocity of a label and the velocity of the DNA molecule. Each wavelength can be associated with multiple slits such that every label has the opportunity to be detected more than once. Multiple detection of the same label allows for the possibility of correction for false-negative and false-positive readings.

Fabrication of Embodiment Nano-Slit Device

Figure 3:
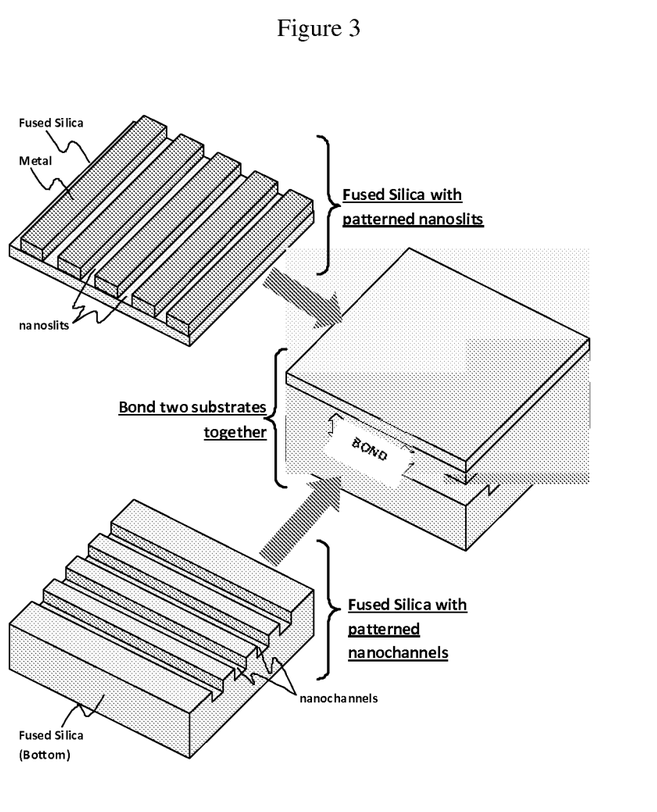
FIG. 3 depicts an exemplary scheme to fabricate a nanoslit device.

One possible fabrication scheme, shown in FIG. 3, is to manufacture the nanoslit embodiment would be to etch an array of nanochannels into the surface of a transparent substrate, such as fused silica or other materials described elsewhere herein. Example processes include photolithography to pattern a film of resist over the substrate, transferring the pattern into the substrate by plasma etching, followed by removal of the resist.

Next, an array of nanoslits composed of metal is patterned on another transparent substrate. Exemplary processes include depositing a metal film over the substrate, then using photolithography to pattern a film of resist over the metal. The resist is used as a mask to etch away the exposed metal, with the resist removed after the metal etching. The matrix device is completed by bonding the array of channels to the array of slits together, orientated orthogonal to each other. Bonding methods include, e.g., fusion bonding, anodic bonding, plasma activated bonding, metal bonding, contact bonding, and the like.

Embodiment: Phase-shift Mask Illumination

Figure 4:
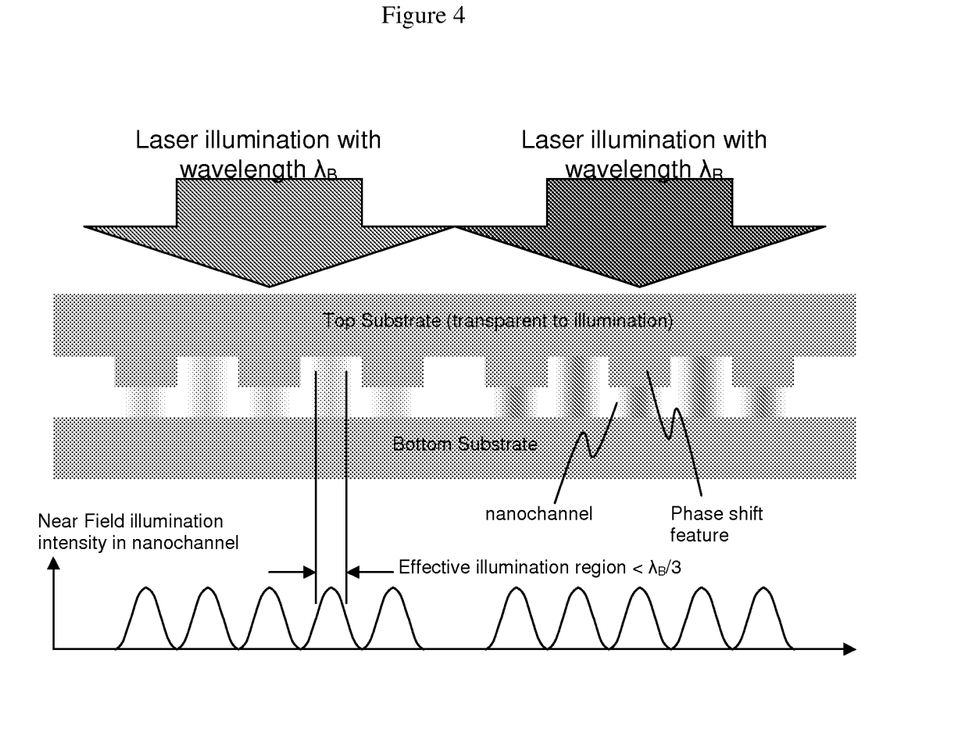
FIG. 4 depicts a sample embodiment whereby the near-field illumination is generated by a phase-shift mask incorporated into the top of the nanochannels.
Figure 5:
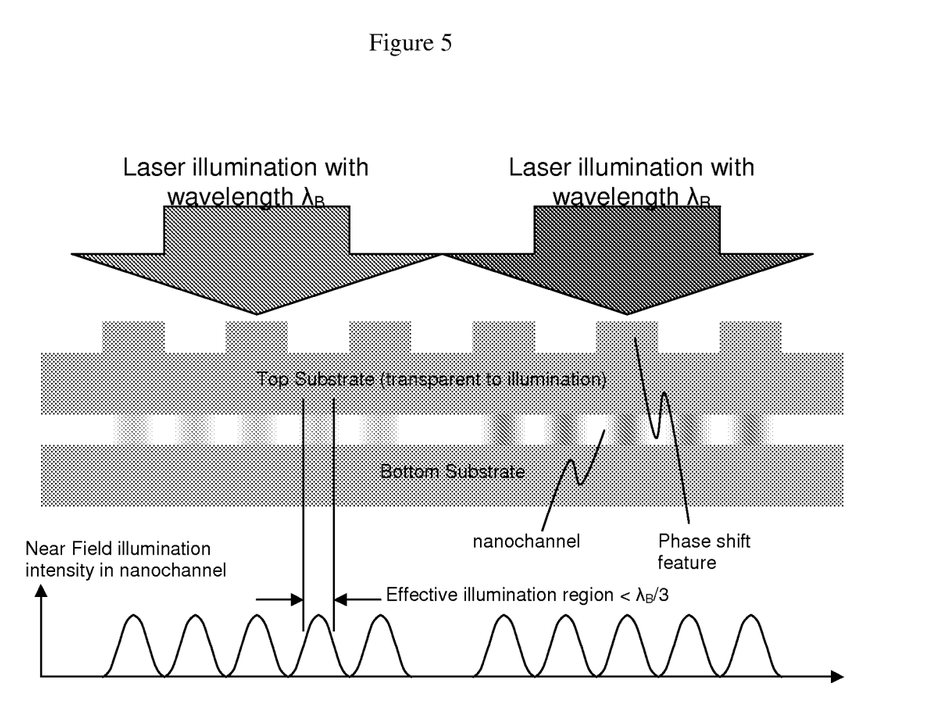
FIG. 5 depicts an embodiment in which the phase-shift mask is patterned on the outside of the substrate.

In this sample embodiment, shown by FIGS. 4 and 5, a phase-shift mask is employed to generate illumination regions within the nanochannel array that are smaller than the wavelength of light used. The width of the illumination region is a function of the wavelength used and phase-shift mask topology, as is well-understood by users of ordinary skill in the art. Illumination regions as small as λ/4 are possible depending on the configuration.

Phaseshift masks are well understood and used within the semiconductor industry to pattern photoresist with features that are smaller than the wavelength of light. As is known in the field, such phaseshift masks take advantage of the interference generated by phase differences to improve image resolution in photolithography.

In another variation, the near-field illumination within the nanochannels can be generated by way of a near-field holography (NFH) mask. One embodiment uses illumination of a NFH grating at 45 degrees. Light incident at an angle is diffracted partially into the minus first (−1) order, and self-interference between the minus first order and the undiffracted zero order creates an interference pattern with a pitch equal to the phase mask pitch. By using a phase shift mask (whether a standard mask or a NFH mask), the user can use the mask to define detection regions within the nanochannel for detection of fluorophores. This is illustrated by non-limiting FIGS. 4 and 5, each of which illustrates a phaseshifting mask in a different configuration. In some embodiments of the present invention, phase shift masks can be used in place of nanoslits or even in combination with nanoslits.

Fabrication of Embodiment Phase Shift

Figure 6:
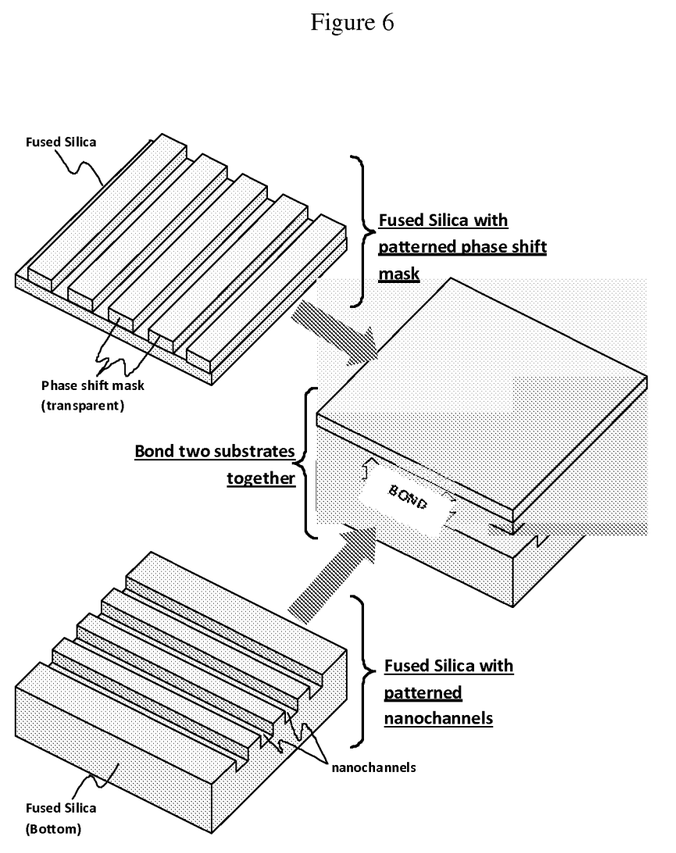
FIG. 6 depicts fabrication of a phase-shifting device.

A phaseshift mask embodiment can be fabricated, as shown in FIG. 6, by bonding (e.g., orthogonally) a substrate patterned with an array of nanochannels to a substrate patterned with an array of phase-shift masks. One method of fabricating the phaseshift mask is to use photolithography to pattern a film of resist over the substrate, then transferring that pattern into the substrate by plasma etching, followed by removal of the resist. The phaseshift mask is then bonded to the nanochannel substrate by fusion bonding, anodic bonding, metal bonding, plasma activated bonding, adhesive bonding, and the like.

Embodiment: Signal Detection and Analysis

In one illustrative embodiment (FIG. 7), as a polymer (e.g., DNA) bearing fluorescent labels passes through the matrix detection region of a nanochannel, the appropriate fluorescent label is excited and fluoresces. This is also shown at, e.g., FIG. 2, where only "blue" flurophores fluoresce when passing by the first nanoslit (which admits illumination that excites only the "blue" fluorophores), only "green" flurophores fluoresce when passing by the second nanoslit (which admits illumination that excites only the "green" fluorophores), and so on.

As shown in FIG. 7, one or more lasers (or other radiation sources) is focused at the bottom of a chip's nanoslits, so as to fluorescently excite the probes on the DNA as the DNA passes over the nanoslits while it flows through the nanochannels. The excited fluorescent signals are detected giving a temporal bar-code signature for each matrix detection region that the DNA passes through. With an appropriate algorithm (e.g., generated by software), these signatures are then translated into a spatial bar-code of the DNA. The bar code sets forth the locations of the various fluorophores on the DNA, which the user can then, in turn, use to arrive at a map of the locations of the various nucleic acid sequences to which the various fluorophores are bound. This knowledge of the locations (or mere presence) of the various sequences yields information about the overall structure of the sample, which structure can be correlated to a condition (or even a likelihood of condition) for the patient/subject.

This will result in the generation of time dependent signals at each matrix location, which are then individually monitored by photo sensors, such as a CCD camera having a matrix of image sensors/pixels.

By monitoring the signal pattern generated from the matrix detection regions of the same wavelength along the same channel, the patterns can be compared to determine which signals correspond to the same fluorophore label on a polymer sample (FIG. 7, inset). In this way, the polymer velocity can be determined. In addition, by detecting the same fluorophore label in multiple matrix detection regions, sufficient redundancy can be achieved such that false-negative and false-positive error correction can be incorporated into the software.

This is shown in additional detail by non-limiting FIG. 8. That figure depicts a matrix device having multiple nanochannels, illuminated by two wavelengths of illumination, with the resulting fluorescence shown at 3 different, successive time intervals (i.e., t0, t1, and t2). Each matrix detection region generates a temporal signal that represents labels of a specific fluorophore passing that region in time. Once the sequence of the labels have been determined for the DNA fragments, this can be used to analyze the DNA. Examples of DNA analysis include structural variation mapping.

In one aspect, the present invention provides analysis devices. Such devices suitably include a plurality of nanochannels running along the surface of a first substrate, each nanochannel defined by side walls and a floor; and at least one nanoslit being disposed in a second substrate, the nanoslit being disposed such that electromagnetic radiation of at least a first wavelength passing through the nanoslit defines, within the at least one nanochannel, an illumination region having a cross-sectional dimension smaller than the first wavelength.

Nanochannels may be fabricated in a variety of ways; U.S. patent application Ser. No. 10/484,793 (the entirety of which is incorporated herein by reference) describes suitable nanochannels and fabrication methods.

In the devices, the first substrate suitable include silica or silicon, both of which materials are well-characterized in the art. Other suitable materials include, e.g., dielectrics, insulators, glass, borofloat glass, sodalime glass, silicon oxynitride, SiOxNy, hydrogenated silicon dioxide, hydrogenated silicon nitride, hydrogenated silicon oxynitride, high K dielectrics, compounds comprising titanium: TiSiO, TiO, TiN, titanium oxides, hydrogenated titanium oxides, titanium nitrides, hydrogenated titanium nitrides, TaO, TaSiO, TaOxNy, Ta2O5, TaCN, tantalum oxides, hydrogenated tantalum oxides, tantalum nitrides, hydrogenated tantalum nitrides, compounds containing hafnium, such as $HfO_2$, $HfSiO_2$, $HfZrO_x$, HfN, HfON, HfSiN, HfSiON, hafnium oxides, hydrogenated hafnium oxides, hafnium nitrides, hydrogenated hafnium nitrides, $ZrO_2$, $ZrSiO_2$, ZrN, ZrSiN, ZrON, ZrSiON, zirconium oxides, hydrogenated zirconium oxides, zirconium nitrides, hydrogenated zirconium nitrides, $Al_2O_3$, AN, TiAlN, TaAlN, WAlN, aluminum oxides, hydrogenated aluminum oxides, aluminum nitrides, hydrogenated aluminum nitrides, SiN, WN, low K dielectrics, fluorine doped silicon dioxide, carbon doped silicon dioxide, porous silicon dioxide, porous carbon doped silicon dioxide, spin-on organic polymeric dielectrics, graphite, graphene, carbon nano-tubes, plastics, polymer, co-polymer, block co-polymer, Polydimethylsiloxane (PDMS), polycarbonate (PC), Poly (methyl methacrylate) (PMMA), Cyclic Olefin Copolymer (COC), a stoichiometric variation of any of the foregoing, or any combination thereof. The user of ordinary skill in the art will encounter little difficulty in identifying the optimal material for a particular application.

Suitably, at least at least one nanochannel is characterized as comprising a width between side walls in the range of from about 10 nm to about 1000 nm. A nanochannel may have such a width of from about 50 nm to about 750 nm, or from about 100 nm to about 500 nm, or from about 200 nm to about 400 nm, or even about 300 nm. Nanochannels are suitably parallel to one another, but may also be intersecting or branched, depending on the needs of the user.

In suitable devices, at least one nanochannel is characterized as comprising a depth from the top of a side wall to the floor of the nanochannel in the range of from about 10 nm to about 1000 nm. The depth may also be in the range of from about 50 nm to about 750 nm, or from about 100 nm to about 500 nm, or from about 200 nm to about 400 nm, or even about 300 nm.

The nearest side walls of at least two adjacent nanochannels are suitably separated by at least about 150 nm, or about 200 nm, about 400 nm, about 500 nm, about 1 micron, about 5 microns, or even about 50 or about 100 microns. Adjacent nanochannels may be even further separated from one another, depending on the needs of the user.

At least one nanoslit is suitably disposed in a second substrate that is opaque to the electromagnetic radiation of at least a first wavelength. The nansolit is suitably of a material different than that of the second substrate, as the electromagnetic radiation suitably passes through the second substrate, and then through the nanoslits. Nanoslit materials suitably include materials opaque to the electromagnetic radiation of interest, including metals (e.g., aluminum, gold, silver, platinum, chrome, titanium, nickel, tungsten, copper, cobalt, Pd, Ir, Fe, Ru, Mn, Mo, V, Nb, Ta, Zr, Hf, La, Y, Sc, Mg, Ca, Sr, Ba, and the like). Polymers, carbon nanotubes, graphite, grapheme, and combinations of any of the foregoing materials are also suitable.

A nanoslit is suitably an aperture characterized as having a cross-sectional dimension less than that of the first wavelength. The nanoslit may be slot-shaped, but may also be ovoid or arc-shaped, and need not necessary have straight edges. The nanoslit aperture suitably has a cross-sectional dimension in the range of from about 1 nm to about 300 nm, or from about 10 nm to about 100 nm, or from about 20 nm to about 70 nm.

The first and second substrates are suitably bonded to one another, and may be of the same or—more suitably—of different materials. The second substrate may comprise silica, silicon, dielectrics, insulators, glass, borofloat glass, sodalime glass, silicon oxynitride, $SiO_xN_y$, hydrogenated silicon dioxide, hydrogenated silicon nitride, hydrogenated silicon oxynitride, high K dielectrics, compounds comprising titanium: TiSiO, TiO, TiN, titanium oxides, hydrogenated titanium oxides, titanium nitrides, hydrogenated titanium nitrides, TaO, TaSiO, $TaO_xN_y$, $Ta_2O_5$, TaCN, tantalum oxides, hydrogenated tantalum oxides, tantalum nitrides, hydrogenated tantalum nitrides, compounds containing hafnium, such as $HfO_2$, $HfSiO_2$, $HfZrO_x$, HfN, HfON, HfSiN, HfSiON, hafnium oxides, hydrogenated hafnium oxides, hafnium nitrides, hydrogenated hafnium nitrides, $ZrO_2$, $ZrSiO_2$, ZrN, ZrSiN, ZrON, ZrSiON, zirconium oxides, hydrogenated zirconium oxides, zirconium nitrides, hydrogenated zirconium nitrides, $Al_2O_3$, AN, TiAlN, TaAlN, WAlN, aluminum oxides, hydrogenated aluminum oxides, aluminum nitrides, hydrogenated aluminum nitrides, SiN, WN, low K dielectrics, fluorine doped silicon dioxide, carbon doped silicon dioxide, porous silicon dioxide, porous carbon doped silicon dioxide, spin-on organic polymeric dielectrics, graphite, graphene, carbon nano-tubes, plastics, polymer, co-polymer, block co-polymer, Polydimethylsiloxane (PDMS), polycarbonate (PC), Poly (methyl methacrylate) (PMMA), Cyclic Olefin Copolymer (COC), a stoichiometric variation of any of the foregoing, or any combination thereof.

The second substrate is suitably transparent to the electromagnetic radiation being applied; it is not always necessary that the first substrate material may not necessarily be similarly transparent. The transparency of the substrates may be dictated by the device configuration; i.e., whether the radiation detector collects light that passes through the first or second substrate. In one suitable design, the detector collects light through the first substrate.]

The devices suitably include a source capable of emitting the electromagnetic radiation of at least a first wavelength. Lasers are one such suitable radiation source.

The radiation source is suitably a device capable of emitting electromagnetic radiation having at least one frequency component in the range of from about 100 nm to about 20,000 nm, or from about 500 nm to about 10,000 nm, or from 1000 nm to about 5000 nm. Frequencies in the range of from about 350 nm to about 1500 nm are considered especially suitable. Radiation sources suitably emit radiation in the visible light or even infrared range. The disclosed devices, however, may suitably function based on radiation in the range of from deep-UV (i.e., appx. 300 nm and below) to about the capability of an exemplary $CO_2$ laser (about 10 microns).

In another aspect, the present invention provides analysis devices. These devices suitably include a plurality of nanochannels running along the surface of a first substrate, each nanochannel being defined by side walls and a floor, a phase mask disposed about at least one nanochannel such that electromagnetic radiation of at least a first wavelength passing through the phase-shift mask defines, in the at least one nanochannel, an illumination region within the at least one nanochannel, the illumination region having a cross-sectional dimension smaller than the first wavelength.

Substrate materials include those described elsewhere herein. Silicon and silicon are considered particularly suitable materials. Nanochannels are suitably of the dimensions set forth elsewhere herein, and are suitably separated as described elsewhere herein.

The phase mask suitably includes a material characterized as essentially transparent to the electromagnetic radiation of at least a first wavelength. In some embodiments, the phase mask includes a near-field holography mask. Such masks are known to those of ordinary skill in the art, and suitably operate by splitting a beam into two such that interfere with each other. Near-field holography masks are considers a sub-set of phase masks. Technically, a NFH mask is sub-set of a phase mask. The phase mask is suitably bonded to the first substrate.

The devices suitably include a source capable of emitting electromagnetic radiation of at least a first wavelength. Such sources include lasers, and suitable wavelengths are set forth elsewhere herein. Other radiation sources, besides lasers, are also considered suitable.

Also provided are methods of analysis. These methods suitably include translocating a macromolecule comprising two or more labels through two or more excitation regions along one or more nanochannels; exciting the labels within the excitation regions with electromagnetic radiation to give rise to one or more signals, the excitation regions being characterized as having a cross-sectional dimension smaller than the wavelength of the electromagnetic radiation; and correlating the one or more signals to the relative positions of the labels along the macromolecule.

The labels are suitably excited using electromagnetic radiation transmitted through a radiation restrictor, such as a nanoslit or other restriction device. Labels include fluorescent dyes, radioactive particles, magnetic particles, and the like; suitable labels are described herein. A label is suitably complementary to a specific region of one or more macromolecules, which in turn enables the user to use labels to discriminate between two or more regions. As one non-limiting example, a label may be bound to a nucleic acid sequence that is itself complementary to a sequence of interest.

In some embodiments, two or more labels are excited by electromagnetic radiation of the same wavelength. In other embodiments, two or more labels are excited by electromagnetic radiation of different wavelengths.

The two or more labels may be excited at different excitation regions. In other embodiments, the two or more labels are excited at the same excitation region.

The methods include correlating signals from two or more labels on two or more macromolecules, and further include correlating the relative positions of the one or more labels to a physiological state, a disease state, or any combination thereof. For example, a user may ascertain the spacing between two regions (e.g., regions x1 and x2) on a sample; if the spacing exceeds the normal spacing between those two regions, the user may conclude that the subject possesses a particular physiological state. As another example, the user may discover that a probe for a particular target sequence binds five times to DNA from a subject; if normal subjects exhibit only zero or one copies of that sequence, the user may have an indication that the subject carries excessive copies of the sequence. This number of copies may in turn suggest that the subject has a particular disease state or is a carrier for a particular disease. The user may also correlate numbers and patterns of markers to physiological states, thus allowing the user to construct a library of physiological states correlated to label/marker presence, against which library the user may compare results from future subjects.

What is claimed is:

1. An analysis device, comprising:
   a plurality of nanochannels running along a surface of a first substrate,
   each nanochannel defined by side walls and a floor; and
   at least two nanoslits being disposed in a second substrate, the nanoslits being disposed such that electromagnetic radiation of at least a first wavelength passing through each nanoslit defines, within the at least one nanochannel, an illumination region having a cross-sectional dimension smaller than the first wavelength of the electromagnetic radiation, whereby the illumination region has a spatial resolution less than a diffraction limit of said electromagnetic radiation.

2. The analysis device of claim 1, wherein the first substrate comprises silica, silicon, dielectrics, insulators, glass, borofloat glass, sodalime glass, silicon oxynitride, $SiO_xN_y$, hydrogenated silicon dioxide, hydrogenated silicon nitride, hydrogenated silicon oxynitride, high K dielectrics, compounds comprising titanium: TiSiO, TiO, TiN, titanium oxides, hydrogenated titanium oxides, titanium nitrides, hydrogenated titanium nitrides, TaO, TaSiO, $TaO_xN_y$, $Ta_2O_5$, TaCN, tantalum oxides, hydrogenated tantalum oxides, tantalum nitrides, hydrogenated tantalum nitrides, compounds containing hafnium: $HfO_2$, $HfSiO_2$, $HfZrO_x$, HfN, HfON, HfSiN, HfSiON, hafnium oxides, hydrogenated hafnium oxides, hafnium nitrides, hydrogenated hafnium nitrides, $ZrO_2$, $ZrSiO_2$, ZrN, ZrSiN, ZrON, ZrSiON, zirconium oxides, hydrogenated zirconium oxides, zirconium nitrides, hydrogenated zirconium nitrides, $Al_2O_3$, AlN, TiAlN, TaAlN, WAlN, aluminum oxides, hydrogenated aluminum oxides, aluminum nitrides, hydrogenated aluminum nitrides, SiN, WN, low K dielectrics, fluorine doped silicon dioxide, carbon doped silicon dioxide, porous silicon dioxide, porous carbon doped silicon dioxide, spin-on organic polymeric dielectrics, graphite, graphene, carbon nano-tubes, plastics, polymer, co-polymer, block copolymer, Polydimethylsiloxane (PDMS), polycarbonate (PC), Poly (methyl methacrylate) (PMMA), Cyclic Olefin Copolymer (COC), a stoichiometric variation of any of the foregoing, or any combination thereof.

3. The analysis device of claim 1, wherein at least one nanochannel is characterized as comprising a width between side walls in the range of from about 10 nm to about 1000 nm.

4. The analysis device of claim 1, wherein at least one nanochannel is characterized as comprising a depth from the top of a side wall to the floor of the nanochannel in the range of from about 10 nm to about 1000 nm.

5. The analysis device of claim 1, wherein each nanoslit is disposed in a second substrate opaque to the electromagnetic radiation of at least a first wavelength.

6. The analysis device of claim 5, wherein the first and second substrates are bonded to one another.

7. The analysis device of claim 1, wherein each nanoslit comprises an aperture characterized as having a cross-sectional dimension less than that of the first wavelength.

8. The analysis device of claim 1, wherein each nanoslit comprises an aperture characterized as having a cross-sectional dimension in the range of from about 1 nm to about 300 nm.

9. The analysis device of claim 1, wherein the second substrate comprises silica, silicon, dielectrics, insulators, glass, borofloat glass, sodalime glass, silicon oxynitride, $SiO_xN_y$, hydrogenated silicon dioxide, hydrogenated silicon nitride, hydrogenated silicon oxynitride, high K dielectrics, compounds comprising titanium: TiSiO, TiO, TiN, titanium oxides, hydrogenated titanium oxides, titanium nitrides, hydrogenated titanium nitrides, TaO, TaSiO, $TaO_xN_y$, $Ta_2O_5$, TaCN, tantalum oxides, hydrogenated tantalum oxides, tantalum nitrides, hydrogenated tantalum nitrides, $HfO_2$, $HfSiO_2$, $HfZrO_x$, HfN, HfON, HfSiN, HfSiON, hafnium oxides, hydrogenated hafnium oxides, hafnium nitrides, hydrogenated hafnium nitrides, $ZrO_2$, $ZrSiO_2$, ZrN, ZrSiN, ZrON, ZrSiON, zirconium oxides, hydrogenated zirconium oxides, zirconium nitrides, hydrogenated zirconium nitrides, $Al_2O_3$, AlN, TiAlN, TaAlN, WAlN, aluminum oxides, hydrogenated aluminum oxides, aluminum nitrides, hydrogenated aluminum nitrides, SiN, WN, low K dielectrics, fluorine doped silicon dioxide, carbon doped silicon dioxide, porous silicon dioxide, porous carbon doped silicon dioxide, spin-on organic polymeric dielectrics, graphite, graphene, carbon nano-tubes, plastics, polymer, co-polymer, block co-polymer, Polydimethylsiloxane (PDMS), polycarbonate (PC), Poly (methyl methacrylate) (PMMA), Cyclic Olefin Copolymer (COC), a stoichiometric variation of any of the foregoing, or any combination thereof.

10. The analysis device of claim 1, further comprising a source capable of emitting the electromagnetic radiation of at least a first wavelength.

11. The analysis device of claim 10, wherein the source comprises a laser.

12. The analysis device of claim 10, wherein the source comprises a device capable of emitting electromagnetic radiation having at least one frequency component in the range of from about 100 nm to about 20,000 nm.

13. An analysis device, comprising:
a plurality of nanochannels running along a surface of a first substrate,
each nanochannel being defined by side walls and a floor; and
a phase-shift mask disposed in at least one of the nanochannels such that electromagnetic radiation of at least a first wavelength passing through the phase-shift mask defines, within the at least one of the nanochannels, an illumination region, wherein the illumination region has a cross-sectional dimension smaller than the first wavelength of the electromagnetic radiation, whereby the illumination region has a spatial resolution less than a diffraction limit of said electromagnetic radiation.

14. The analysis device of claim 13, wherein the substrate comprises silica, silicon, dielectrics, insulators, glass, borofloat glass, sodalime glass, silicon oxynitride, $SiO_xN_y$, hydrogenated silicon dioxide, hydrogenated silicon nitride, hydrogenated silicon oxynitride, high K dielectrics, compounds comprising titanium: TiSiO, TiO, TiN, titanium oxides, hydrogenated titanium oxides, titanium nitrides, hydrogenated titanium nitrides, TaO, TaSiO, $TaO_xN_y$, $Ta_2O_5$, TaCN, tantalum oxides, hydrogenated tantalum oxides, tantalum nitrides, hydrogenated tantalum nitrides, $HfO_2$, $HfSiO_2$, $HfZrO_x$, HfN, HfON, HfSiN, HfSiON, hafnium oxides, hydrogenated hafnium oxides, hafnium nitrides, hydrogenated hafnium nitrides, $ZrO_2$, $ZrSiO_2$, ZrN, ZrSiN, ZrON, ZrSiON, zirconium oxides, hydrogenated zirconium oxides, zirconium nitrides, hydrogenated zirconium nitrides, $Al_2O_3$, AlN, TiAlN, TaAlN, WAlN, aluminum oxides, hydrogenated aluminum oxides, aluminum nitrides, hydrogenated aluminum nitrides, SiN, WAlN, low K dielectrics, fluorine doped silicon dioxide, carbon doped silicon dioxide, porous silicon dioxide, porous carbon doped silicon dioxide, spin-on organic polymeric dielectrics, graphite, graphene, carbon nano-tubes, plastics, polymer, co-polymer, block co-polymer, Polydimethylsiloxane (PDMS), polycarbonate (PC), Poly (methyl methacrylate) (PMMA), Cyclic Olefin Copolymer (COC), a stoichiometric variation of any of the foregoing, or any combination thereof.

15. The analysis device of claim 13, wherein at least one nanochannel is characterized as comprising a width between side walls in the range of from about 10 nm to about 300 nm.

16. The analysis device of claim 13, wherein at least one nanochannel is characterized as comprising a depth from the top of a side wall to the floor of the nanochannel in the range of from about 10 nm to about 1000 nm.

17. The analysis device of claim 13, wherein the phase-shift mask comprises a material essentially transparent to the electromagnetic radiation of at least a first wavelength.

18. The analysis device of claim 13, further comprising a source capable of emitting electromagnetic radiation of at least a first wavelength.

19. The analysis device of claim 18, wherein the source comprises a laser.

20. The analysis device of claim 18, wherein the source comprises a device capable of emitting electromagnetic radiation having at least one frequency component of from about 100 nm to about 20,000 nm.

21. The analysis device of claim 13, wherein the phase-shift mask comprises a near-field holography mask.

22. The analysis device of claim 13, wherein the phase-shift mask is bonded to the first substrate.

23. The analysis device of claim 13, wherein the cross-sectional dimension of the illumination region is smaller than ⅓ of the first wavelength of the electromagnetic radiation.

24. A method of analysis, comprising:
providing an analysis device comprising:
a plurality of nanochannels running along a surface of a first substrate, each nanochannel defined by side walls and a floor; and
at least two nanoslits being disposed in a second substrate, the nanoslits being disposed such that electromagnetic radiation of at least a first wavelength passing through each nanoslit defines, within the at least one nanochannel, an illumination region having a cross-sectional dimension smaller than the first wavelength of the electromagnetic radiation, whereby the illumination region has a spatial resolution less than a diffraction limit of said electromagnetic radiation;
translocating a macromolecule comprising two or more labels through two or more illumination regions along one or more nanochannels;
exciting the labels within the illumination regions with electromagnetic radiation to give rise to one or more signals;
detecting the one or more signals from the illumination regions; and
correlating the one or more detected signals to the relative positions of the labels along the macromolecule.

25. The method of claim 24, wherein the labels are excited using electromagnetic radiation transmitted through a radiation restrictor.

26. The method of claim 24, wherein a label comprises a fluorescent dye.

27. The method of claim 24, wherein one or more labels are complementary to a specific region of one or more macromolecules.

28. The method of claim 24, wherein two or more labels are excited by electromagnetic radiation of the same wavelength.

29. The method of claim 24, wherein two or more labels are excited by electromagnetic radiation of different wavelengths.

30. The method of claim 29, wherein the two or more labels are excited at different excitation regions.

31. The method of claim 24, further comprising correlating signals from two or more labels on two or more macromolecules.

32. The method of claim 24, further comprising correlating the relative positions of the one or more labels to a physiological state, a disease state, or any combination thereof.

* * * * *